United States Patent [19]

Cichanowicz et al.

[11] Patent Number: 4,888,287

[45] Date of Patent: * Dec. 19, 1989

[54] RAPID DIFFERENTIATION OF FUNGI FROM BACTERIA USING POLYENE ANTIBIOTICS

[75] Inventors: Peggy W. Cichanowicz, Pittsford; Robert T. Belly, Webster, both of N.Y.

[73] Assignee: Eastman Kodak Company, Rochester, N.Y.

[ * ] Notice: The portion of the term of this patent subsequent to Dec. 5, 2006 has been disclaimed.

[21] Appl. No.: 910,923

[22] Filed: Sep. 24, 1986

[51] Int. Cl.[4] .................................................. C12Q 1/04
[52] U.S. Cl. ...................................... 435/34; 435/29; 435/31; 435/38; 435/39; 435/805; 435/810
[58] Field of Search ....................... 435/29, 31, 34, 38, 435/39, 805, 810

[56] References Cited

U.S. PATENT DOCUMENTS

| | | | |
|---|---|---|---|
| 3,870,600 | 3/1975 | Youssef | 435/34 |
| 4,140,580 | 2/1979 | Gibson et al. | 435/34 |
| 4,525,453 | 6/1985 | Guardino et al. | 435/34 |
| 4,746,607 | 5/1988 | Mura et al. | 435/25 |

OTHER PUBLICATIONS

Fingold et al., "Bailey and Scott's Diagnostic Microbiology" C. V. Mosby Co., St. Louis 1978, p. 21.
Garrod et al., "Antibiotic and Chemotherapy" Churchill Livingstone, Edinburgh and London, 1973, pp. 228–232.

*Primary Examiner*—Robert Benson
*Attorney, Agent, or Firm*—J. Lanny Tucker

[57] ABSTRACT

Rapid differentiation between viable fungi (for example, yeast) and viable bacteria is accomplished with certain polyene antibiotics which are used in combination with a compound which is normally reducible by both the fungi and the bacteria. The antibiotics selectively and substantially inhibit the reduction of the reducible compound by the fungi but do not affect the reducing capacity of the bacteria. The particular antibiotics useful are polyenes which selectively affect the function of the cytoplasmic membrane of fungi.

20 Claims, No Drawings

RAPID DIFFERENTIATION OF FUNGI FROM BACTERIA USING POLYENE ANTIBIOTICS

FIELD OF THE INVENTION

The present invention relates to clinical chemistry. It particularly relates to a composition, element and method for differentiation between viable fungi and viable bacteria.

BACKGROUND OF THE INVENTION

The detection and identification of microorganisms are important for health maintenance and diagnostic care. Current detection and identification procedures are based on culturing the organisms. Such procedures are labor intensive and time consuming and require skilled personnel and special equipment.

The detection and differentiation of fungi from bacteria are generally performed by growth enrichment techniques in selective culture media, as described, for example, in U.S. Pat. No. 4,140,580 (issued February 20, 1979 to Gibson et al). This reference teaches the use of specific components in the culture media that inhibit the growth of bacterial organisms while yeast and fungi continue to grow and are detected by a subsequent color change.

However, the procedures of the art, including that of U.S. Pat. No. 4,140,580, require 12 to 18 hours for completion. This lost time may be critical to the proper treatment of illnesses, or to the adjustment of manufacturing processes. It would be highly desirable to have a rapid process for identifying fungi which is simple to use and can be readily automated.

SUMMARY OF THE INVENTION

The problems noted above with known procedures are avoided with a composition for differentiating between viable fungi and bacteria comprising:

(a) a compound capable of being reduced to a detectable species by both viable fungi and bacteria in the absence of reduction-inhibiting materials, and (b) a polyene antibiotic which affects the function of the cytoplasmic membrane, the antibiotic being present in an amount sufficient to selectively and substantially inhibit the reduction of the reducible compound by the fungi.

The present invention also provides an analytical element for differentiating between viable fungi and bacteria comprising an absorbent carrier material and containing:

(a) a compound capable of being reduced to a detectable species by both viable fungi and bacteria in the absence of reduction-inhibiting materials, and (b) a polyene antibiotic which affects the function of the cytoplasmic membrane, the antibiotic being present in an amount sufficient to selectively and substantially inhibit the reduction of the reducible compound by the fungi.

Further, a method for differentiating between viable fungi and bacteria comprises the steps of:

A. mixing a liquid suspected of containing viable fungi and bacteria with (a) a compound capable of being reduced to a detectable species by both viable fungi and bacteria in the absence of reduction-inhibiting materials, and (b) a polyene antibiotic which affects the function of the cytoplasmic membrane, the antibiotic being present in an amount sufficient to selectively and substantially inhibit the reduction of the reducible compound by the fungi, and B. determining the detectable species resulting from the presence of the bacteria.

The present invention provides a rapid, simple and relatively inexpensive means for differentiating viable fungi from viable bacteria. This invention avoids the undesirably tedious features of known techniques. Further, a wide variety of reducible compounds can be used thereby giving flexibility in the assay. For example, such flexibility allows the use of dyes which have high sensitivity, are less toxic to living materials or which can be detected in spectral regions not affected by potential interferents found in biological or other fluids. These advantages are achieved by using polyene antibiotics which selectively affect the cytoplasmic membrane of fungi in combination with a reducible compound.

DETAILED DESCRIPTION OF THE INVENTION

The present invention is useful for the determination of fungi, both unicellular organisms, such as yeasts, and multicellular organisms, such as molds. This invention is preferably practiced to differentiate yeast from bacteria.

The antibiotics useful in the practice of this invention are those known in the art as polyenes antibiotics. However, not every polyene antibiotic is useful in the practice of this invention. Useful polyene antibiotics are those which primarily affect the function of the cytoplasmic membrane of the organisms as opposed to antibiotics which primarily interfere with nucleic acid or protein biosynthesis or which interfere with cell wall biosynthesis. Such materials are described in a text by R. Reiner entitled *Antibiotics*, Thieme-Stratton, New York, 1982 for example, at pages 57, 60 and 131–132. Polyene antibiotics useful in the practice of this invention are generally understood to be antibiotics having a multiplicity (two or more) of conjugated double bond linkages. Further details of polyene antibiotics and methods of synthesis are described in Chapter 8 (pages 207–229) of *Biochemistry and Genetic Regulation of Commercially Important Antibiotics* edited by Leo C. Vining, Addison-Wesley Publishing, Reading, Massachusetts, U.S.A., 1983 and the references noted therein.

Without intending to be so limited in the practice of this invention, the following polyene antibiotics are useful in the practice of this invention: nystatin, natamycin, amphotericin B, candicidin, filipin, hachimycin, pecilocin, and partricin. Preferred antibiotics include filipin and nystatin.

It will be understood by those skilled in the art that for each antibiotic useful in the present invention there will be optimal concentration range, depending on the purity and potency of the antibiotic, and environmental conditions for inhibiting the reductive capability of fungi and for differentiation. Further, there may be a few exceptions to the selective inhibitory action of the polyene antibiotics to certain bacteria or fungi.

In general, the amount of antibiotic needed to selectively and substantially inhibit the reduction of the reducible compound by fungi can be determined readily by mixing about $10^7$ cells/ml of fungi (for example, *Candida albicans*), and antibiotic (about $10^{-4}$ molar), a reducible compound (about 0.005 molar) at pH 7.5. If the reducible compound is reduced producing a detectable change, the amount of antibiotic is increased accordingly in subsequent tests until no detectable change is observed.

The reducible compound useful in the practice of this invention can be any material that, in its oxidized form, is capable of being reduced by both viable bacteria (either gram-positive and gram-negative) and fungi, in the absence of any reduction-inhibiting materials, to produce a detectable species. Such species can be detected by any suitable means including potentiometric or radiometric means. Preferably, as defined below, the species is detected with radiometric means.

A partial listing of various detectable species that are directly detectable by radiometric means includes chromogens, fluorogens, chemiluminescent materials, radioactive isotopes, phosphorescent materials and others known to one skilled in the art.

The use of dyes, or generally, dye precursors, as the detectable species is preferred. The use of a dye or dye precursors presents several possibilities for detection: (1) a colored species can become colorless or undergo a shift in absorption, (2) a colorless species, for example, a dye precursor can form a colored species, or (3) a species containing a shiftable detectable species can release the shiftable detectable species. Alternative (3) is preferred in the practice of this invention.

Examples of dyes or dye precursors that can be used as reducible compounds include methylene blue, dichloroindophenol, resazurin, and various tetrazolium compounds, such as 3-(4,5-dimethyl-2-thiazolyl)-2,5-diphenyl-2H-tetrazolium bromide, 2,3,5-triphenyl-2H-tetrazolium chloride, tetranitro blue, tetrazolium chloride and nitrotetrazolium violet, and others described, for example in U.S. Pat. No. 4,525,453 (issued June 25, 1985 to Guardino et al).

More particularly, the reducible compounds useful in this invention have the structure CAR—(R$^1$)$_n$ wherein CAR— represents a substituted or unsubstituted aromatic or quinone nucleus, R$^1$ is a moiety comprising a shiftable detectable species defined herein, and n is 1 or 2. The term "shiftable detectable species" can be defined as a chromogen moiety which has a first spectral absorption band while attached to the reducible compound and a second spectral absorption band when released, or as a fluorogen moiety which has first spectral absorption and emission bands while attached and second spectral absorption and emission bands when released. Examples of such nuclei are presented below. Further, when R$^1$ is replaced by H, CAR—(H)$_n$ has a a reduction potential (E$_{\frac{1}{2}}$) of either at least about +100 mV when measured in water, or of at least about −650 mV when measured in acetonitrile.

Reduction of the compound and subsequent release of the detectable species is achieved at physiological pH (that is, 9 or less) because the compound has the appropriate E$_{\frac{1}{2}}$ value. Such measurements are made according to standard electrochemical techniques using either polarography or cyclic voltametry (see, for example, Sawyer and Roberts, Jr., *Experimental Electrochemistry for Chemists*, John Wiley & Sons, New York, 1974). Preferably, the E$_{\frac{1}{2}}$ is from about +100 mV to about +400 mV as measured in water, or from about −650 to about −300 mV as measured in acetonitrile. Both ranges are given because some of the reducible compounds are best measured in water whereas others are best measured in acetonitrile. Further details of measuring the E$_{\frac{1}{2}}$ are described below prior to Table I. The desired E$_{\frac{1}{2}}$ is achieved by appropriate electron withdrawing groups on the CAR-nucleus, or by a strained fused ring attached to the nucleus or by a combination of both.

In one embodiment, the reducible compounds can be reduced to provide a detectable species through quinone methide formation, similar to the description by Van de Sande in *Angew. Chem. Int. Ed. Engl.* 22, pp. 191–209 (1983) and U.S. Pat. No. 4,232,107 (issued November 4, 1980 to Janssens), but which have the desired E$_{\frac{1}{2}}$ properties.

In another embodiment, useful reducible compounds include sulfilimides and sulfenylsulfonamides similar to those described on page 206 of the Van de Sande reference noted above, but which have the desired E$_{\frac{1}{2}}$ properties.

In a preferred embodiment, the reducible compounds are RIND compounds, that is, reducible compounds capable of undergoing intramolecular nucleophilic displacement at physiological pH to release one or more detectable species when a nucleophilic group is generated by at least a one electron reduction of the compound. In other words, such displacement occurs when the RIND compound is reduced by a suitable reductant which provides the necessary electron(s) (described in more detail below). The release of detectable species is very efficient in that, for most of the preferred compounds, at least 50% of the detectable species is provided within 30 minutes at about pH 7.

The term "intramolecular nucleophilic displacement" refers to a reaction in which a nucleophilic center on a molecule reacts at another site in the molecule, which site is an electrophilic center, to effect displacement of a group or atom attached to the electrophilic center. Generally, the RIND compounds useful in this invention have the nucleophilic and electrophilic groups juxtaposed in the three-dimensional configuration of the molecule in close proximity whereby the intramolecular reaction can take place and a ring is formed having from 4 to 7 atoms, and preferably having 5 or 6 atoms.

Particularly useful RIND compounds are those represented by the structure CAR—R$^1$ wherein CAR— is

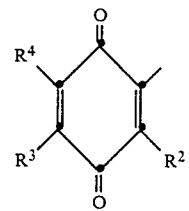

R$^1$ is

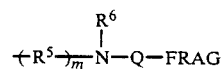

wherein m is 0 or 1, and preferably 1. R$^5$ is substituted or unsubstituted alkylene, preferably of 1 or 2 carbon atoms in the backbone (for example, methylene, ethylene or alkoxymethylene). Most preferably, R$^5$ is methylene. Q is carbonyl or thiocarbonyl and preferably carbonyl.

R$^6$ is substituted or unsubstituted alkyl, preferably of 1 to 40 carbon atoms (for example, methyl, ethyl, n-propyl, isopropyl, t-butyl, hexyl, decyl, lauryl or benzyl), substituted or unsubstituted cycloalkyl, preferably of 4 to 40 carbon atoms (for example, cyclobutyl, cyclohexyl or 4-methylcyclohexyl), substituted or unsubstituted heterocycle, preferably of 5 to 40 atoms (carbon and heteroatoms, for example, pyridyl), or substituted or unsubstituted aryl, preferably of 6 to 40 carbon atoms (for example, phenyl, xylyl, naphthyl, p-nitrophenyl, anthryl, p-t-butoxyphenyl or p-carboxyphenyl). Preferably, $R^6$ is substituted or unsubstituted alkyl, or substituted or unsubstituted aryl as defined above.

FRAG is a shiftable detectable species as defined above. The specific composition of FRAG can vary considerably depending upon the type of detectable species desired and upon the particular detection means employed. The detectable species can be a material which is directly detectable by a suitable means, as well as a material which can react with other substances, for example, analytes, enzymes or other reagents to provide a detectable species.

Particularly useful detectable species are chromogens and fluorogens. Examples of useful classes of chromogens are azo, azomethine, nitrophenol, indophenol, indoaniline and triarylmethane dyes, and others known in the art, with azo dyes being preferred. Examples of useful classes of fluorogens are coumarin, umbelliferone, phenalenone and benzphenalenone, 4-oxo-4-H-benz-[d, e]anthracenes, fluorescein and rhodamine fluorescent dyes, and others known in the art. Phenalenone dyes are particularly useful.

Useful phosphorescent species include such phosphors as 2',5'-dibromofluorescein and 4',5'-diiodofluorescein. A useful chemiluminescent species is luciferin.

FRAG is linked to Q by means of a single bond through a bivalent monoatom linkage which is a part of FRAG. Preferably, the monoatom linkage is oxy, thio or seleno, and most preferably it is oxy. However, when FRAG is a fluorogen, the linkage is oxy or thio.

$R^2$, $R^3$ and $R^4$ in the above quinone structure are independently hydrogen, substituted or unsubstituted alkyl of 1 to 40 carbon atoms (for example, methyl, ethyl, hydroxymethyl or methoxymethyl) substituted or unsubstituted aryl (for example, phenyl, naphthyl, methylnaphthyl, p-nitrophenyl, m-methoxyphenyl or p-carboxyphenyl) or an electron withdrawing group which generally has a positive Hammett sigma value, and preferably has a sigma value greater than about 0.06. At least one of $R^2$, $R^3$ and $R^4$ is an electron withdrawing group. Hammett sigma values are calculated in accordance with standard procedures described, e.g. in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (for example, fluoro, bromo, chloro or iodo), trihalomethyl (for example, trifluoromethyl or trichloromethyl), trialkylammonium, carbonyl, carbamoyl, sulfonyl, sulfamoyl, esters and others known in the art, or alkyl or aryl groups (defined above) substituted with one or more of these electron withdrawing groups. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ can also be $R^1$ thereby potentially providing a 2:1 molar ratio of detectable species molecules to original RIND compound molecules.

Alternatively, $R^3$ and $R^4$, taken together, can represent the carbon atoms necessary to complete a substituted or unsubstituted stained fused carbocyclic ring attached to the quinone nucleus. Strained fused rings are known in the art (for example, Reike et al, *Tetrahedron Letters*, 50, pp. 4381–4384, 1969). For example, such a ring (mono- or bicyclic) can have from 4 to 8 carbon atoms in the backbone. Preferably, the ring is a 5-membered mono-ring, or a 7- or 8-membered bicyclic ring.

Particularly useful reducible compounds are the water-compatible compounds described and claimed in copending and commonly assigned U.S. Ser. No. 868,855, filed May 30, 1986 by Mura et al and entitled WATER-COMPATIBLE REDUCIBLE COMPOUNDS AND THEIR USE IN ANALYTICAL COMPOSITIONS AND METHODS.

Representative RIND compounds are listed in Table I below in reference to the following structure:

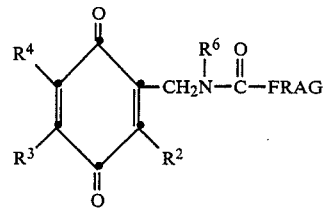

The $E_{\frac{1}{2}}$ values in Table I were determined for the quinone nucleus of this structure having a hydrogen atom in place of

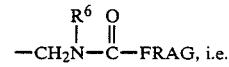

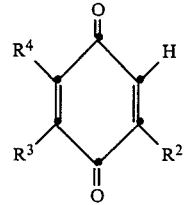

The $E_{\frac{1}{2}}$ values (where available) were measured in an aqueous emulsion of the quinone dissolved in N,N-dimethylformamide, a nonionic surfactant (for example, TRITON X-100) and sodium phosphate buffer (pH 7). A standard calomel electrode was used as a standard. Some $E_{\frac{1}{2}}$ values (denoted by *) were measured in acetonitrile using a saturated calomel electrode as a standard. $E_{\frac{1}{2}}$ values not available are denoted by "NA".

TABLE I

| RIND Compound | $R^6$ | $R^2$ | $R^4$ | $R^3$ | FRAG | $E_1$ (mV) |
|---|---|---|---|---|---|---|
| I. | $-CH_3$ | $-CH(CH_3)$-C₆H₄-SO$_2$NHC$_{10}$H$_{21}$ | same as $R^2$ | $-CH_2N(CH_3)$-C(O)-FRAG | [naphthol-azo-(SO$_2$CH$_3$, NO$_2$)-phenyl with NHSO$_2$-C₆H₄-SO$_2$NH$_2$] | −528* |
| II. | $-CH_3$ | $-CH(CH_3)$-C₆H₄-NO$_2$ | " | " | " | +236 |
| III. | $-CH_3$ | $-CH(CH_3)$-C₆H₄-SO$_2$NHCH(CH$_3$)$_2$ | " | " | " | NA |
| IV. | $-CH_3$ | -C₆H₅ | " | " | " | −460* |
| V. | $-CH_3$ | -C₆H₄-NO$_2$ | \multicolumn{2}{l|}{$R^3$ and $R^4$ together form [cyclic]} | " | +214 |
| VI. | $-CH_3$ | -C₆H₅ | \multicolumn{2}{l|}{"} | " | +180 |

TABLE I-continued
| RIND Compound | R⁶ | R² | R⁴ | R³ | FRAG | E½ (mV) |
|---|---|---|---|---|---|---|
| VII. | —CH₃ | 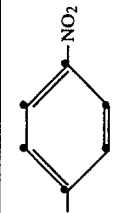 | | " | " | +236 |
| VIII. | —CH₃ | 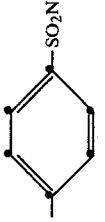 | | " | " | +212 |
| IX. | —CH₃ |  | | " | " | +220 |
| X. | —CH₃ | 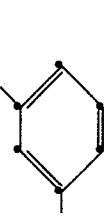 | | " | " | +154 |
| XI. | —CH₃ | 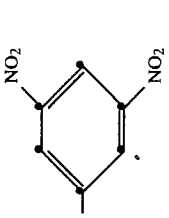 | | " | " | +186 |
| XII. | —CH₃ | 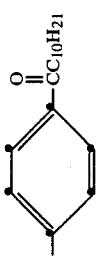 | | " | " | +206 |
| XIII. | —CH₃ |  | | " | " | +212 |

TABLE I-continued

| RIND Compound | R$^6$ | R$^2$ | R$^4$ | R$^3$ | FRAG | E$_{\frac{1}{2}}$ (mV) |
|---|---|---|---|---|---|---|
| XIV. | —CH$_3$ | (4-Br-phenyl) | " | " | " | +192 |
| XV. | —CH$_3$ | —H | " | " | " | +213 |
| XVI. | —C$_{12}$H$_{25}$ | (4-CN-phenyl) | " | " | " | +220 |
| XVII. | —CH$_3$ | " | R$^3$ and R$^4$ together form (cyclopentene) | | " | +240 |
| XVIII. | —CH$_3$ | (4-NO$_2$-phenyl) | —t-butyl | —H | " | NA |
| XIX. | —CH$_3$ | (phenyl) | R$^3$ and R$^4$ together form (cyclopentadiene) | | " | +242 |
| XX. | —CH$_3$ | " | R$^3$ and R$^4$ together form (cyclopentene) | | " | +222 |

TABLE I-continued

| RIND Compound | R⁶ | R² | R⁴ | R³ | FRAG | $E_{\frac{1}{2}}$ (mV) |
|---|---|---|---|---|---|---|
| XXI. | —CH₃ | —CH(CH₃)(phenyl-SO₂NHC₁₀H₂₁) | same as R² | —CH₂N(CH₃)—C(O)—FRAG | naphthyl-azo-phenyl(SO₂NH₂), NHSO₂CH₃, —O⁻ substituents | −528* |
| XXII. | —CH₃ | " | " | " | chromene-type structure with CH₃ | −528* |
| XXIII. | —CH₃ | phenyl-NO₂ | R³ and R⁴ together form cyclic | | " | +214 |
| XXIV | —CH₃ | phenyl-Cl,Cl | R³ and R⁴ together form cyclic | | naphthyl-azo-phenyl(SO₂CH₃, NO₂), NHSO₂-phenyl-SO₂NH₂, —O⁻ | +236 |
| XXV. | —CH₃ | —phenyl | R³ and R⁴ together form C₁₂H₂₅ | | " | +222 |

TABLE I-continued

| RIND Compound | R⁶ | R² | R⁴ | R³ | FRAG | $E_{\frac{1}{2}}$ (mV) |
|---|---|---|---|---|---|---|
| XXXVI. | —CH₃ | " | —CH₃ | —CH₃ | " | +144 |
| XXXVII. | —CH₃ | " | R³ and R⁴ together form (CH₃-cyclopentyl ring) | | " | +122 |
| XXVIII. | —CH₃ | " | R³ and R⁴ together form ((CH₃)₂HC-, CH₃ substituted ring) | | " | +174 |
| XXIX. | —CH₃ | 4-CN-phenyl | R³ and R⁴ together form (cyclopentyl ring) | | (methoxy-phenalenone) | +220 |
| XXX. | —CH₃ | phenyl | R³ and R⁴ together form | | " | +222 |
| XXXI. | —CH₃ | 2,4-diCl-phenyl | R³ and R⁴ together form | | " | +236 |

TABLE I-continued

| RIND Compound | R[6] | R[2] | R[4] | R[3] | FRAG | $E_{\frac{1}{2}}$ (mV) |
|---|---|---|---|---|---|---|
| XXXII. | —CH$_3$ | —C$_6$H$_4$—NO$_2$ | R$^3$ and R$^4$ together form cyclopentene ring | | " | +214 |
| XXXIII. | —CH$_3$ | —C$_6$H$_4$—NO$_2$ | | | " | +236 |
| XXXIV. | —CH$_3$ | —C$_6$H$_4$—SO$_2$NH(CH$_3$)$_2$ | | | " | +212 |
| XXXV. | —CH$_3$ | —C$_6$H$_4$—COOH | | | " | +220 |

RIND compound XXXV is preferred in the practice of this invention.

The RIND compounds useful in the practice of this invention are prepared using a sequence of individually known reactions. Generally, the preparation sequence includes the following general steps: (1) preparation of the substituted hydroquinone, (2) oxazine ring formation, (3) oxazine ring opening, (4) preparation of the carbamoyl chloride, and (5) reaction of a compound from which the FRAG moiety is derived with the carbamoyl chloride. Preparation of these compounds is described in more detail in copending and commonly assigned U.S. Ser. No. 824,766, filed January 31, 1986 by Belly et al and entitled REDUCIBLE COMPOUNDS AND ANALYTICAL COMPOSITIONS, ELEMENTS AND METHODS UTILIZING SAME. The preparation of Compound XXXV is described in U.S. Ser. No. 868,855, noted above.

Other RIND compounds useful in the practice of this invention include those having the appropriate $E_{\frac{1}{2}}$ values and the structure CAR—$(R^1)_n$ wherein:

(1) CAR— is a substituted or unsubstituted nucleus of a 1,2-naphthoquinone, 1,2-, 1,4- or 9,10-anthraquinone, 4,4'-diphenoquinone, azuloquinone or 1,6-[10]-anulenoquinone wherein $R^1$ is attached to the nucleus one carbon atom distant or in the peri position from one of the oxo groups of the nucleus. The nucleus can be substituted with one or more electron withdrawing groups as described above for $R^2$ or have one or more fused rings as described above for $R^3$ and $R^4$.

$R^1$ is

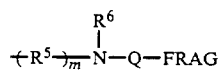

as defined above, and n is an integer of 1 or 2.

(2) CAR— is

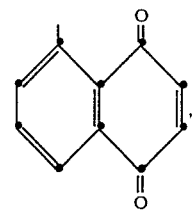

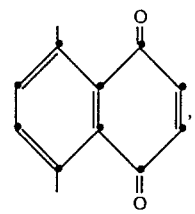

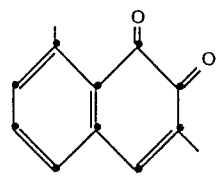

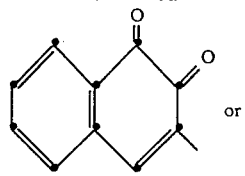

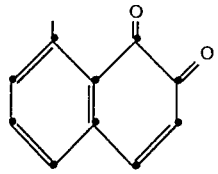

any of which can be substituted with one or more electron withdrawing groups as described above for $R^2$, $R^3$ and $R^4$. $R^1$ is

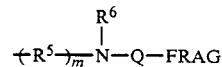

as defined above, and n is 1 or 2.

(3) CAR— is a substituted or unsubstituted nitrobenzenoid nucleus of the structure

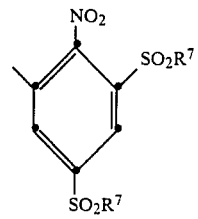

wherein $R^7$ is substituted or unsubstituted alkyl of 1 to 20 carbon atoms (for example, methyl, ethyl, methoxymethyl, isopropyl, dodecyl, hexadecyl or octadecyl), and $R^1$ is

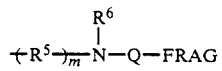

as defined above and n is 1. These compounds are similar to some described in U.S. Pat. No. 4,139,379 (noted above).

In another embodiment, the reducible compound can be a cobalt (III) complex, as described in copending and commonly assigned U.S. Ser. No. 890,050, filed by Schmittou July 28, 1986 and entitled COBALT CONTAINING REAGENTS AND METHODS FOR THE DETERMINATION OF ANALYTES IN AQUEOUS FLUIDS.

All of these reducible compounds can be prepared using techniques and starting materials known in the art or readily apparent to a skilled synthetic chemist.

Generally, many of the reducible compounds described herein have limited water solubility. Hence, it is best, when using them in an aqueous environment, to prepare a dispersion of the compound prior to use, for example, in a coating formulation. Such dispersions generally comprise the reducible compound, an aqueous buffer solution and either a solubilizing surfactant or a water-miscible organic solvent for the compound, or both. Surfactants which are useful in the practice of this invention include any surfactants which do not inhibit compound reduction. Nonionic surfactants are particularly useful.

Useful water-miscible organic solvents include alcohols (for example, methanol, ethanol or propanol), N,N-dimethylformamide, dimethyl sulfoxide, acetonitrile, hexamethylenephosphoramide and others known in the art. The particular solvent to be used for a particular reducible compound can be readily determined by routine experimentation.

A dispersion can be prepared in the following general manner. The reducible compound is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10 ml surfactant per ml of dispersion. This preparation is generally carried out at room temperature.

These dispersions generally are effectively buffered to maintain a pH of 9 or less. The concentration of buffer in the dispersion can vary widely but is generally at least about 0.01. Representative buffers include phosphates and others reported by Good et al in *Biochemistry*, 5, 467 (1966), and *Anal. Biochem.*, 104, 300 (1980).

When using water-compatible reducible compounds, solutions can be prepared without surfactants by dissolving the compound in an organic solvent described above, and adding the resulting solution directly to a buffer.

The present invention is useful for differentiation of viable fungi from both gram-positive and gram-negative bacteria in any fluid specimen including wastewater, food stuffs, brewing solutions, manufacturing solutions and biological fluids. It is particularly useful in differentiation of yeast from microorganisms in human biological fluids, such as urine, serum, whole blood, sputum, spinal fluid and others known to one skilled in the art. Organisms commonly found in the human urinary tract are advantageously differentiated with this invention.

Differentiation of viable organisms according to this invention is preferably carried out in the presence of an electron transfer agent (identified herein as an ETA). The presence of an ETA provides more rapid dye release. It is a mobile compound which acts as an intermediary between the organism and the reducible compound. The ETA is generally present at a concentration that is dependant upon the concentration of the reducible compound, but preferably at a concentration of from about $1 \times 10^{-7}$ molar to about $1 \times 10^{-3}$ molar.

ETA compounds useful in the practice of this invention include phenazine methosulfate, phenazine ethosulfate and similar compounds known to one skilled in the art. Combinations of different ETA compounds can be used if desired.

Preferred ETA compounds are those which are the subject of copending and commonly assigned U.S. Ser. No. 699,374 of Mura et al filed February 7, 1985, now U.S. Pat. No. 4,746,607. In general, those compounds are substituted benzo- and naphthoquinones. Examples of this class of quinones include 2,3-dimethyl-5-hydroxymethyl-1,4-benzoquinone, 2,5-dimethoxy-1,4-benzoquinone, 2,3,5-trimethyl-1,4-benzoquinone, 2,6-dimethoxy-1,4-benzoquinone, 2,3-dimethoxy-5-methyl-1,4-benzoquinone, 2-hydroxymethyl-1,4-naphthoquinone and 2-(2-hydroxyethyl)-1,4-naphthoquinone. Substituted 1,2-benzoquinones, such as 4,5-dimethoxy-1,2-benzoquinone, are also useful in the practice of this invention.

The differentiation of viable cells is often carried out in the presence of a nutrient for those cells although its presence is not essential. Any nutrient medium can be used which contains useful carbon, and optionally nitrogen, sources. Suitable nutrient media having proper components and pH are well known in the art.

The polyene antibiotic concentration can also vary widely depending upon the antibiotic and reducible compound used, as well as the particular organisms being differentiated as long as it is sufficient to inhibit the reductive capacity of the fungi but not the gram-positive and gram-negative bacteria. Generally, the antibiotic is present in an amount of at least about $10^{-5}$, and preferably from about $10^{-4}$ to about $10^{-2}$, molar. The other preferred but optional materials are present in amounts which one skilled in the art can readily determine with routine experimentation.

The method of this invention can conveniently be carried out in standard laboratory glassware, for example, using test tubes, slides or microtitration plates. The fungi and bacteria in a liquid specimen are mixed with the reducible compound, the polyene antibiotic and any other materials as required. After an appropriate time for reduction of the reducible compound by the organisms, the amount of detectable species resulting from reduction is measured with suitable equipment and procedures. The amount of detectable species can then, if desired, be compared to the amount produced in a control test where the liquid specimen is mixed with the reducible compound, but the antibiotic is omitted.

In a preferred embodiment, a liquid specimen is tested first with a reducible compound to determine the presence of microorganisms. Then, it is tested with a polyene antibiotic composition of this invention to distinguish between fungi and bacteria, followed by differentiation between gram-positive and gram-negative bacteria. This bacterial differentiation can be carried out using any suitable technique. Preferred techniques are described and claimed in U.S. Ser. No. 910,917 filed on even date herewith by Cichanowicz et al and entitled RAPID DIFFERENTIATION OF BACTERIA USING POLYETHER ANTIBIOTICS and in copending and commonly assigned U.S. Ser. No. 910,703 filed on even data herewith by Cichanowicz et al and entitled RAPID DIFFERENTIATION OF BACTERIA USING CYCLIC POLYPEPTIDE ANTIBIOTICS.

In some instances, it may be desirable to mix and incubate the test sample containing fungi and bacteria and the antibiotic in a pretreatment step prior to mixing with the reducible compound therein. This may reduce the amount of background density encountered with some assays due to the presence of impurities in the antibiotics. Another pretreatment step to eliminate interferents may also be desirable.

The method can also be carried out by contacting a porous absorbent material, e.g. paper strip, containing a test sample with a dispersion of the reducible compound and polyene antibiotic. The microorganisms in the test sample can intermingle with the dispersion and initiate the analytical reactions needed for differentiation.

In one embodiment, a test strip can be used as a convenient way to carry measured amounts of reagent(s) to the test solution in a solution assay. The test strip is placed into a solution that might already contain the analyte to be measured. The reagents dissolve from the test strip into the solution so as to form the reaction solution. In preferred embodiments of the test strips of the present invention, the reagents are carried in a water soluble binder. When the test strip is immersed into the solution, the binder dissolves releasing the reagents. Useful water soluble polymers include poly(N-vinyl-2-pyrrolidone) and poly(acrylamide-co-N-vinyl-2-pyrrolidone) (90:10 weight ratio).

Alternatively, the method of this invention can be practiced with a dry analytical element. Such an element can be a absorbent carrier material, that is, a thin sheet or strip of self-supporting absorbent or bibulous material, such as filter paper or strips, which contains the reducible compound and antibiotic or a dried residue of same. Such elements are known in the art as test strips, diagnostic elements, dip sticks, diagnostic agents and the like.

When employed in dry analytical elements, the reducible compounds and antibiotics described herein can be incorporated into a suitable absorbent carrier material by imbibition or impregnation, or can be coated on a suitable absorbent material. Useful carrier materials are insoluble and maintain their structural integrity when exposed to water or physiological fluids such as urine or serum. Useful carrier materials can be prepared from paper, porous particulate structures, cellulose, porous polymeric films, glass fiber, woven and nonwoven fabrics (synthetic and nonsynthetic) and the like. Useful materials and procedures for making such elements are well known in the art as exemplified by U.S. Pat. Nos. 3,092,465 (issued June 4, 1963 to Adams et al), 3,802,842 (issued April 9, 1974 to Lange et al), 3,915,647 (issued October 28, 1975 to Wright), 3,917,453 (issued November 4, 1975 to Milligan et al), 3,936,357 (issued February 3, 1976 to Milligan et al), 4,248,829 (issued February 3, 1981 to Kitajima et al), 4,255,384 (issued March 10, 1981 Kitajima et al), and 4,270,920 (issued June 2, 1981 to Kondo et al), and U.K. Pat. No. 2,052,057 (published January 21, 1981).

In one embodiment, an analytical element comprises a nonporous support having thereon at least one porous spreading zone as the absorbent carrier material. The reducible compound or antibiotic can be in the spreading zone or in a different zone (for example, a reagent zone, registration zone or hydrophilic zone). The spreading zone can be prepared from any suitable fibrous or non-fibrous material or mixtures of either or both.

The spreading zone can be prepared using fibrous materials, either mixed with a suitable binder material or woven into a fabric, as described in U.S. Pat. No. 4,292,272 (issued September 29, 1981 to Kitajima et al), from polymeric compositions or particulate materials, with or without binding adhesives, as described in U.S. Pat. Nos. 3,992,158 (issued November 16, 1976 to Przybylowicz et al), 4,258,001 (issued March 24, 1981 to Pierce et al) and 4,430,436 (issued February 7, 1984 to Koyama et al) and Japanese Patent Publication No. 57(1982)-101760 (published June 24, 1982). It is desired that the spreading zones be isotropically porous, meaning that the porosity is the same in each direction in the zone as created by interconnected spaces or pores between particles, fibers or polymeric strands.

Suitable supports can be any suitable dimensionally stable, and preferably, transparent (that is, radiation transmissive) film or sheet material which transmits electromagnetic radiation of a wavelength between about 200 and about 900 nm. A support of choice for a particular element should be compatible with the intended mode of detection (for example, reflection, fluorescence or transmission spectroscopy) and inert to chemical reagents and liquid samples used in the assay. Useful support materials include polystyrene, polyesters, polycarbonates, cellulose esters and others known in the art.

The elements can have a multiplicity of zones which can be superposed layers or distinct areas in the same layer. The reducible compound, antibiotic and any other reagents can be located in the same or different zones within the element. Element configurations are well known in the art, as described, for example in the patents noted above.

A variety of different elements can be prepared in accordance with the present invention. Elements can be configured in a variety of forms, including elongated tapes of any desired width, sheets, slides or chips.

The method carried out with an element can be manual or automated. In general, differentiation is made by taking the element from a supply roll, chip packet or other source and contacting it with a sample (for example up to 200 $\mu$l) of the liquid to be tested so that the sample mixes with the reagents in the element. Such contact can be accomplished in any suitable manner, for example, dipping or immersing the element into the sample or, preferably, by spotting the element by hand or machine with one or more drops of the sample with a suitable dispensing means.

After sample application, the element can be exposed to conditioning, such as incubation, heating or the like, that may be desirable to quicken or otherwise facilitate obtaining any test result. Detection of viable fungi cells is achieved when the amount of reducible compound reduced is determined and compared to the amount of detectable species produced in the absence of antibiotic. In some instances, the antibiotic and test sample may be mixed and pretreated (as described above for a solution assay) prior to applying the mixture to the element containing the reducible compound.

Materials used in the following examples were obtained as follows:

gram-negative microorganism *Escherichia coli* (ATCC 25922), gram-positive microorganism *Staphylococcus aureus* (ATCC 25923), and *Candida albicans* yeast cells (ATCC 14053), brain heart infusion broth (BHI) and Sabaroud's dextrose broth (SAB) from Difco Laboratories (Detroit, Michigan, U.S.A.), and *Aspergillus flavus* (ATCC 20047), a mold from American Type Culture Collection (Rockville, Maryland, U.S.A.).

nystatin, amphotericin B and filipin antibiotics from Sigma Chemical Co. (St. Louis, Missouri, U.S.A.), natamycin and candicidin antibiotics from USPC, Inc. (Rockville, Maryland, U.S.A.), TRITON X-100 nonionic surfactant from Rohm and Haas (Philadelphia, Pennsylvania, U.S.A.), trimethyl-1,4-benzoquinone from the corresponding hydroquinone purchased from Aldrich Chemical Co. (Milwaukee, Wisconsin, U.S.A.), and the remainder from Eastman Kodak Co. (Rochester, New York, U.S.A.) or prepared using known starting materials and procedures.

In practicing the method of this invention, the following procedures were carried out:

E. coli and S. aureus were grown overnight in BHI broth at 37° C. C. albicans and A. flavus were grown overnight at 25° C. in SAB broth with agitation. The cells were harvested by centrifugation, washed and resuspended in 0.05 molar N-2-hydroxyethylpiperazine-N'-2-ethanesulfonic acid (HEPES) buffer (pH 7.8).

Dispersions containing RIND compounds were prepared by dissolving, for example, RIND VII from Table I above in N,N-dimethylformamide (DMF) at 16 mg compound per ml of solvent. An aliquot (250 μl) of the resulting solution was added to 500 μl of TRITON X-100 surfactant. This mixture was then added dropwise with stirring to 25 ml of 0.05 molar HEPES buffer. A solution containing a water-compatible RIND compound (for example, RIND XXXV) was prepared by dissolving the compound in N,N-dimethylformamide which had been acidified with 0.1% sulfuric acid (16 mg RIND compound per ml of solvent).

EXAMPLE 1

Differentiation of Yeast from Bacteria

This example demonstrates the practice of this invention to differentiate viable yeast from both viable gram-positive and gram-negative bacteria in solution.

The following materials were used in this example: stock solutions of RIND IX compound dispersion prepared as described above, glucose (10% in water), trimethyl-1,4-benzoquinone ETA (1.5 mg/ml methanol), and the antibiotics (25 mg/ml in dimethyl sulfoxide, except that filipin was 12.5 mg/ml of solvent). Bacteria and yeast were grown as described above. The approximate final cell concentrations in the assay mixture were $4.2 \times 10^8$ cells/ml of E. coli, $7.1 \times 10^8$ cells/ml of S. aureus, and $7 \times 10^5$ of C. albicans.

The tests were run as follows:

Method 1:

Test solutions were prepared by adding in order: 1.2 ml of HEPES buffer, 50 μl glucose solution, 1.5 ml of RIND IX dispersion, 100 μl of antibiotic solution, 100 μl of cell suspension and 25 μl of ETA solution. Cell control solutions contained all reagents except antibiotics. Background controls consisted of both buffer and solution controls. The buffer control contained all reagents except antibiotics and cells. The solution control contained all reagents except cells. Optical density readings (OD) were measured at 635 nm at 0 minutes and after incubation at 37° C. for 30 minutes for test and Control solutions, and the change in density (ΔOD) was determined. Table II below lists the results, expressed as corrected percent inhibition of the reduction of the RIND compound. The corrected percent inhibition is calculated by dividing the difference between the ΔOD obtained from the Control without antibiotic and the ΔOD of the test solution, by ΔOD of the Control without antibiotic. All readings were corrected by subtracting readings of the appropriate background control.

Method 2:

Solutions containing 2.9 ml HEPES, 50 μl of the antibiotic solution, and 100 μl cell solution were incubated at 37° C. for 30 minutes, centrifuged for 10 minutes and decanted. The resulting pellet was then treated with 1.4 ml HEPES, 50 μl glucose solution, 1.5 ml RIND IX dispersion and 25 μl ETA solution, mixed well and the optical densities recorded as described above in Method 1. The corrected percent inhibition data was calculated as described in Method 1 above.

The data in Table II below indicates that the polyene antibiotics are effective in differentiating yeast cells from the gram-positive and gram-negative microorganisms.

TABLE II

| Antibiotic | Test Method | Corrected % Inhibition | | |
|---|---|---|---|---|
| | | C. albicans | E. coli | S. aureus |
| Nystatin | 1 | 76.2 | No Inhibition | 9.8 |
| Natamycin | 1 | 77.9 | No Inhibition | 0.3 |
| Amphotericin B | 1 | 74.1 | 15.1 | No Inhibition |
| Candicidin* | 2 | 62.8 | 12.5 | No Inhibition |
| Filipin | 2 | 97.5 | No Inhibition | No Inhibition |

*Preincubation for 1 hour.

EXAMPLE 2

Differentiation of Yeast and Mold from Bacteria

This example demonstrates the practice of the present invention for differentiation of a yeast and a mold from both gram-negative and gram-positive bacteria using a water-compatible RIND compound. The differentiations were run in microtitration plates.

A composition was prepared from the following components: 100 μl RIND XXXV solution (16 mg RIND compound per ml of acidified N,N-dimethylformamide), 200 μl glucose solution (10% in water), 200 μl trimethyl-1,4-benzoquinone ETA solution (1.5 mg/ml methanol) and 10 ml HEPES buffer.

Test solutions were prepared using the following reagents: 50 μl HEPES buffer, 50 μl filipin polyene antibiotic (12.5 mg/ml dimethylsulfoxide) (serial dilutions of buffer and antibiotic solutions were performed to obtain various antibiotic concentrations), 50 μl of the appropriate cell suspensions, that is, E. coli (about $10^8$ cells/ml), S. aureus (about $10^8$ cells/ml), C. albicans (about $10^7$ cells/ml) and A. flavus, and 200 ml of the RIND composition described above.

Control solutions were prepared as described in Example 1. Relative fluorescence was measured using a Dynatech MICROFLUOR Reader (Dynatech Laboratories, Alexandria, Virginia) modified to read at excitation 540 nm and emission 620 nm, at zero time and after incubation at 37° C. for 30 minutes. The change in relative fluorescence was then determined as the difference of the two values.

Table III below shows the results obtained, expressed as corrected percent inhibition of the reduction of the RIND compound, which were calculated as described in Example 1.

These results demonstrate the usefulness of the present invention to differentiate fungi (e.g. mold and yeast) from bacteria.

TABLE III

| Antibiotic (Filipin) Concentration (mg/ml) | Corrected Percent Inhibition | | | |
|---|---|---|---|---|
| | E. coli (gram −) | S. aureus (gram +) | C. albicans (yeast) | A. flavus (mold) |
| 0.26 | 0 | 7.5 | 56.8 | 31.9 |
| 0.52 | 0 | 8.6 | 71.0 | 42.5 |
| 1.04 | 2.0 | 14.8 | 80.7 | 49.8 |
| 2.08 | 17.6 | 18.2 | 86.8 | 64.9 |

EXAMPLE 3

Differentiation of Yeast and Mold From Bacteria Using a Tetrazolium Salt

This example demonstrates the practice of the present invention using a tetrazolium salt as the reducible compound.

The differentiations of yeast and mold from bacteria were carried out in microtitration plates. The cell suspensions used were like those described in Example 2. The reducible compound used was 3-(4,5-dimethyl-2-thiazolyl)-2,5-diphenyl-2H-tetrazolium bromide (MTT). A composition containing MTT was prepared with the following components: 200 μl MTT solution (5 mg/ml methanol), 200 μl glucose solution (10% glucose in water), 200 μl trimethyl-1,4-benzoquinone ETA and 12 ml of HEPES buffer (0.05 molar, pH 7.8).

Test solutions were prepared using the following components: 50 μl HEPES buffer, 50 μl filipin polyene antibiotic (12.5 mg/ml dimethylsulfoxide) (serial dilutions of buffer and antibiotic solutions were performed to obtain various antibiotic concentrations), 50 μl of the appropriate cell suspension, i.e. $E.\ coli$ (about $10^8$ cells/ml), $S.\ aureus$ (about $10^8$ cells/ml), $C.\ albicans$ (about $10^7$ cells/ml) and $A.\ flavus$, and 200 ml of the MTT composition noted above. Cell Controls contained all reagents except the antibiotic. Background was measured with buffer. Solution Controls contained all reagents except cells.

Optical density measurements were made at 540 nm using a commercially available spectrophotometer, and the change in optical density (ΔOD) was determined after 30 minutes at 37° C. Table IV below shows the results expressed as corrected percent inhibition which was calculated as described in Example 1 above. These results demonstrate the usefulness of the present invention for differentiation of yeast and mold from bacteria. It is apparent that the concentration effective for differentiation of yeast is different than for mold. However, it is well within the skill of a worker in the art to determine the appropriate concentration for a given test.

TABLE IV

| Antibiotic (Filipin) Concentration (mg/ml) | Corrected Percent Inhibition | | | |
|---|---|---|---|---|
| | E. coli (gram −) | S. aureus (gram +) | C. albicans (yeast) | A. flavus (mold) |
| 0.26 | 0 | 0 | 10.3 | 0 |
| 0.52 | 0 | 0 | 50.0 | 10.3 |
| 1.04 | 0 | 0 | 60.3 | 19.0 |
| 2.08 | 0 | 0 | 100 | 98.3 |

EXAMPLE 4

Differentiation of Yeast and Bacteria Using a Dry Element

This example demonstrates the practice of the present invention for differentiation of yeast and bacteria using a dry analytical element.

Strips of commercially available 3 mm chromatography paper were washed twice with acetone and then immersed in a test solution containing the following components: 6 ml methanol, 1 ml RIND XXXV solution (16 mg/ml acidified N,N-dimethylformamide prepared as described above), 1 ml 2,3-dimethoxy-5-methyl-1,4-benzoquinone ETA solution (1.82 mg/ml methanol), 1 ml glucose solution (10% in water) and 1 ml of filipin polyene antibiotic solution (25 mg/ml dimethylsulfoxide). A Control solution was prepared having the same components except the antibiotic and separated strips were immersed therein. All strips were then dried in a darkened area at 25° C. for one hour.

A standard paper punch was used to cut circular elements (about 0.6 cm in diameter) from the dried strips. The elements were then placed in microtitration plates. Samples (10 μl) of cells suspensions (i.e. $C.\ albicans$, about $5 \times 10^7$ cells/ml, $E.\ coli$, about $5 \times 10^8$ cells/ml and $S.\ aureus$, about $5 \times 10^8$ cells/ml) were applied to both test elements and Control elements. Buffer solution was applied to separate elements for background readings.

Relative fluorescence (excitation at 540 nm and emission at 620 nm) was measured using a Dynatech MICROFLUOR reader at zero time and after 30 minutes incubation at 37° C., and the change in relative fluorescence was determined. Table V below shows the results obtained as corrected percent inhibition which was calculated as described in Example 1 above. These results show that the assay using a dry element differentiated yeast from bacteria according to the present invention.

TABLE V

| Organism | Corrected Percent Inhibition |
|---|---|
| S. aureus (gram +) | 0 |
| E. coli (gram −) | 18 |
| C. albicans (yeast) | 76 |

The invention has been described in detail with particular reference to preferred embodiments thereof, but it will be understood that variations and modifications can be effected within the spirit and scope of the invention.

We claim:

1. A composition for differentiating between viable fungi and bacteria comprising
    (a) a dye or dye precursor capable of being reduced to a detectable species by both viable fungi and bacteria, and
    (b) a polyene antibiotic which affects the cytoplasmic membrane, said antibiotic being present in an amount sufficient to selectively and substantially inhibit the reduction of said reducible dye or dye precursor by said fungi.

2. The composition of claim 1 further comprising an electron transfer agent.

3. The composition of claim 1 wherein said antibiotic is selected from the group consisting essentially of nystatin, natamycin, amphotericin B, candicidin and filipin.

4. The composition of claim 1 further comprising a cell nutrient containing useful carbon.

5. The composition of claim 1 wherein said reducible dye or dye precursor is represented by the structure CAR─(R$^1$)$_n$ wherein CAR— is a carbocyclic aromatic or quinone nucleus, R$^1$ is a moiety which comprises a shiftable detectable species which is either a chromogen having a first spectral absorption band while attached to said nucleus and a second spectral absorption band when released, or a fluorogen having first spectral absorption and emission bands while attached to said nucleus and second spectral absorption and emission bands when released, and n is 1 or 2, provided said reducible dye or dye precursor is capable of being reduced at physiological pH to release said shiftable detectable species, and further provided that when $R^1$ is replaced with H, CAR—(H)$_n$ has an $E_{\frac{1}{2}}$ of either at least about $+100$ mV when measured in water, or of at least about $-650$ mV when measured in acetonitrile.

6. The composition of claim 5 wherein said reducible dye precursor has the structure CAR—$R^1$ wherein CAR— is

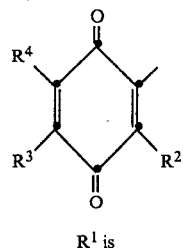

$R^1$ is

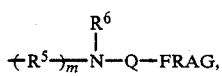

$R^2$ and $R^4$ are independently hydrogen, alkyl, carbocyclic aryl or an electron withdrawing group having a positive Hammett sigma value, $R^3$ is $R^1$, hydrogen, alkyl, carbocyclic aryl or an electron withdrawing group having a positive Hammett sigma value, provided at least one of $R^2$, $R^3$ and $R^4$ is an electron withdrawing group having a positive Hammett sigma value, or $R^3$ and $R^4$, taken together, represent the atoms necessary to complete a nonaromatic, strained fused carbocyclic 4- to 8-membered ring, $R^5$ is alkylene of 1 or 2 carbon atoms, $R^6$ is alkyl, cycloalkyl, pyridyl, or carbocyclic aryl, Q is carbonyl or thiocarbonyl, FRAG is said shiftable detectable species which provides a detectable species when released from said reducible dye precursor upon reduction by viable bacteria, and m is 0 or 1, provided that when $R^1$ is replaced with H, CAR—H has an $E_{\frac{1}{2}}$ of either at least about $+100$ mV when measured in water, or of at least about $-650$ mV when measured in acetonitrile.

7. The composition of claim 6 wherein FRAG provides a chromogen or fluorogen.

8. An analytical element for differentiating between viable fungi and bacteria comprising an absorbent carrier material and containing:
(a) a dye or dye precursor capable of being reduced to a detectable species by both viable fungi and bacteria, and
(b) a polyene antibiotic which affects the cytoplasmic membrane, said antibiotic being present in an amount sufficient to selectively and substantially inhibit the reduction of said reducible dye or dye precursor by said fungi.

9. The element of claim 8 further comprising an electron transfer agent.

10. The element of claim 8 wherein said antibiotic is selected from the group consisting essentially of nystatin, natamycin, amphotericin B, candicidin and filipin.

11. The element of claim 8 further comprising a cell nutrient containing useful carbon.

12. The element of claim 8 wherein said reducible dye or dye precursor is represented by the structure CAR—(R$^1$)$_n$ wherein CAR— is a carbocyclic aromatic or quinone nucleus, $R^1$ is a moiety which comprises a shiftable detectable species which is either a chromogen having a first spectral absorption band while attached to said nucleus and a second spectral absorption band when released, or a fluorogen having first spectral absorption and emission bands while attached to said nucleus and second spectral absorption and emission bands when released, and n is 1 or 2, provided said reducible dye or dye precursor is capable of being reduced at physiological pH to release said shiftable detectable species, and further provided that when $R^1$ is replaced with H, CAR—(H)$_n$ has an $E_{\frac{1}{2}}$ of either at least about $+100$ mV when measured in water, or of at least about $-650$ mV when measured in acetonitrile.

13. The element of claim 12 wherein said reducible dye precursor has the structure CAR—$R^1$ wherein CAR— is

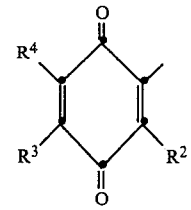

$R^1$ is

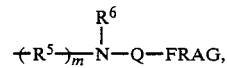

$R^2$ and $R^4$ are independently hydrogen, alkyl, carbocyclic aryl or an electron withdrawing group having a positive Hammett sigma value, $R^3$ is $R^1$, hydrogen, alkyl, carbocyclic aryl or an electron withdrawing group having a positive Hammett sigma value, provided at least one of $R^2$, $R^3$ and $R^4$ is an electron withdrawing group having a positive Hammett sigma value, or $R^3$ and $R^4$, taken together, represent the atoms necessary to complete a nonaromatic, strained fused carbocyclic 4- to 8-membered ring, $R^5$ is alkylene of 1 or 2 carbon atoms, $R^6$ is alkyl, cycloalkyl, pyridyl, or carbocyclic aryl, Q is carbonyl or thiocarbonyl, FRAG is said shiftable detectable species which provides a detectable species when released from said reducible dye precursor upon reduction by viable bacteria, and m is 0 or 1, provided that when $R^1$ is replaced with H, CAR—H has an $E_{\frac{1}{2}}$ of either at least about $+100$ mV when measured in water, or of at least about $-650$ mV when measured in acetonitrile.

14. A method for differentiating between viable fungi and bacteria comprising the steps of:
A. mixing a first sample of a liquid suspected of containing viable fungi or viable bacteria with a dye or dye precursor capable of being reduced to a detectable species by both said fungi and said bacteria,
B. mixing a second sample of said liquid with
(a) said dye or dye precursor, and
(b) a polyene antibiotic which affects the cytoplasmic membrane, said antibiotic being present in an amount sufficient to selectively and substantially inhibit the reduction of said reducible dye or dye precursor by said fungi, and C. measuring the difference between said detectable species resulting from steps A and B.

15. The method of claim 14 wherein said liquid is also mixed with an electron transfer agent and a cell nutrient containing useful carbon.

16. The method of claim 14 wherein said antibiotic is selected from the group consisting essentially of nystatin, natamycin, amphotericin B, candicidin and filipin.

17. The method of claim 14 wherein said detectable species is determined colorimetrically or fluorometrically.

18. The method of claim 14 wherein said reducible dye or dye precursor is represented by the structure CAR$\pm$(R$^1$)$_n$ wherein CAR— is a carbocyclic aromatic or quinone nucleus, R$^1$ is a moiety which comprises a shiftable detectable species which is either a chromogen having a first spectral absorption band while attached to said nucleus and a second spectral absorption band when released, or a fluorogen having first spectral absorption and emission bands while attached to said nucleus and second spectral absorption and emission bands when released, and n is 1 or 2, provided said reducible dye or dye precursor is capable of being reduced at physiological pH to release said shiftable detectable species, and further provided that when R$^1$ is replaced with H, CAR$\pm$(H)$_n$ has an E$_{\frac{1}{2}}$ of either at least about +100 mV when measured in water, or of at least about −650 mV when measured in acetonitrile.

19. The method of claim 18 wherein said reducible dye precursor has the structure CAR—R$^1$ wherein CAR— is

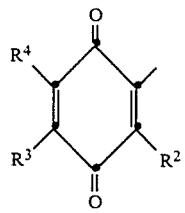

R$^1$ is $$+R^5\!\!\rightarrow_{\overline{m}}\!\!\underset{\underset{R^6}{|}}{N}\!-\!Q\!-\!FRAG,$$

R$^2$ and R$^4$ are independently hydrogen, alkyl, carbocyclic aryl or an electron withdrawing group having a positive Hammett sigma value, R$^3$ is R$^1$, hydrogen, alkyl, carbocyclic aryl or an electron withdrawing group having a positive Hammett sigma value, provided at least one of R$^2$, R$^3$ and R$^4$ is an electron withdrawing group having a positive Hammett sigma value, or R$^3$ and R$^4$, taken together, represent the atoms necessary to complete a nonaromatic, strained fused carbocyclic 4- to 8-membered ring, R$^5$ is alkylene of 1 or 2 carbon atoms, R$^6$ is alkyl, cycloalkyl, pyridyl, or carbocyclic aryl, Q is carbonyl or thiocarbonyl, FRAG is said shiftable detectable species which provides a detectable species when released from said reducible dye precursor upon reduction by viable bacteria, and m is 0 or 1, provided that when R$^1$ is replaced with H, CAR—H has an E$_{\frac{1}{2}}$ of either at least about +100 mV when measured in water, or of at least about −650 mV when measured in acetonitrile.

20. A method for detecting the presence of bacterial cells in a liquid biological specimen, differentiating any bacterial cells present in said specimen from fungi in said specimen, and differentiating between gram-negative and gram-positive bacterial cells in said specimen, comprising the steps of:

(i) mixing a first sample of said specimen with a dye or dye precursor capable of being reduced to a detectable species by both said fungi and said bacteria, (ii) mixing a second sample of said specimen with
 (a) said dye or dye precursor and
 (b) a polyene antibiotic which affects the cyto plasmic membrane, said antibiotic being present in an amount sufficient to selectively and substantially inhibit the reduction of said reducible dye or dye precursor by said fungi, (iii) measuring the difference between said detectable species resulting from steps A and B to differentiate between said bacteria and said fungi, and (iv) differentiating between gram-positive and gram-negative bacteria in a third sample of said specimen.

* * * * *